United States Patent [19]

Austin et al.

[11] 4,284,834

[45] Aug. 18, 1981

[54] DIETHYNYL AROMATIC HYDROCARBONS WHICH HOMOPOLYMERIZE AND CHAR EFFICIENTLY AFTER CURE

[75] Inventors: William B. Austin, Gardena; Norman Bilow, Encino, both of Calif.

[73] Assignee: Hughes Aircraft Company, Culver City, Calif.

[21] Appl. No.: 106,621

[22] Filed: Dec. 26, 1979

[51] Int. Cl.³ .............................................. C07C 15/16
[52] U.S. Cl. ..................................................... 585/25
[58] Field of Search ........................................ 585/25

[56] References Cited

U.S. PATENT DOCUMENTS

| | | | |
|---|---|---|---|
| 3,749,700 | 7/1973 | Stephens et al. | 585/25 |
| 3,756,982 | 9/1973 | Korshak et al. | 585/25 |
| 4,016,214 | 4/1977 | Douglas et al. | 585/25 |
| 4,172,100 | 10/1979 | Tung et al. | 585/25 |
| 4,181,684 | 1/1980 | Sigwalt et al. | 585/25 |

*Primary Examiner*—Veronica O'Keefe
*Attorney, Agent, or Firm*—Booker T. Hogan, Jr.; William H. MacAllister

[57] ABSTRACT

Diethynyl substituted aromatic hydrocarbons are prepared which homopolymerize into resins suitable for use as high char materials.

7 Claims, No Drawings

DIETHYNYL AROMATIC HYDROCARBONS WHICH HOMOPOLYMERIZE AND CHAR EFFICIENTLY AFTER CURE

TECHNICAL FIELD

This invention relates generally to the preparation of homopolymerizable aromatic hydrocarbons and more particularly to the preparation of diethynyl substituted aromatic hydrocarbons which char efficiently to provide high density, carbonized structures when used as impregnants for graphite fibrous cloths.

BACKGROUND OF THE INVENTION

The need for light weight ablative materials for aerospace and military applications is well established. Petroleum and coal tar pitches are currently used as carbon matrix precursors in the fabrication of carbon-carbon composites. The Air Force baseline, high density composite matrix precursor, has been ALLIED CHEMICAL COMPANY's 15 V coal tar pitch. While this material has provided acceptable properties in carbon-carbon composites, there are disadvantages in its use. Some of these are:
1. variable composition and properties;
2. difficulty in processing;
3. impurities which are variable in quantity and composition;
4. low char yield, in low pressure processing; and
5. uncertainty in future availability.

The variable composition of the 15 V pitch is the result of its derivation from a fossil fuel which is variable both in its organic origin and in its final state. The inorganic ash impurity content also is highly variable.

The lack of constancy of pitch compositions in general is reflected in variations in properties such as viscosity, char yield, gaseous decomposition products, and the nature of the char, such as porosity, hardness, and morphology. Attempts to improve processibility of coal tar pitches by pretreatment procedures have been helpful, but have not solved all of the problems indicated.

Ash content variations of pitches, such as 15 V, very likely affect such factors in a composite as matrix crystallinity, porosity, and strength as well as the char yield. The quinoline insoluble fraction of pitches (QI's) varies widely and inorganic substances affect ablation performance adversely through the char structure, conversion of char to graphite, or by catalyzing the oxidation of the graphite in air.

In addition to the petroleum and coal tar pitches, aromatic heterocyclic polymers have also been available in recent years. They include both condensation polymers such as the polybenzimidazoles, pyrrones, polyimides, polyquinoxalines, addition type polymers such as acetylene-substituted polyimides (for example Thermid 600 or HR600), acetylene-terminated quinoxaline (ATQ), bismaleimides (P13N and P105A), Michael-addition type polyimides (Kerimide) and "polymerized monomeric reactants" (PMR).

Several of these polymers are good char formers after they are fully cured, but those that cure by condensation evolve large volumes of gaseous by-products during the cure. Furthermore, since these materials are not processable after cure, (for example polyimides, PBI, pyrrone) they must be processed in their prepolymeric outgassing form. In addition, volatile solvents are required during processing. As a consequence, if used to produce 3-D carbon-carbon structures, these latter polymers liberate large volumes of gases before and during pyrolysis, thus yielding very porous structures.

Addition-type polymers such as HR600, P13N, and P105A are theoretically better suited for the 3D carbon-carbon applications, but their melting points are too close to their cure temperatures and thus they do not remain fluid for a sufficiently long period of time at their melting points to allow them to be effectively processed in the 3-D carbon-carbon applications.

The closest art to the present invention known to the inventors involves the use of prepolymers of diethynylbenzene. One of these materials was sold as "H resin" by Hercules Chemical Co. of Wilmington, Del., although it has since been removed from the market. "H resin" was sold as a high char forming laminating resin, however, its cure was too difficult to control. "H resin" was a solid polymer rather than a low melting low viscosity material. Thus, it was sold as a polymer solution. In this form, when used to impregnate a woven 3-D graphite fabric, all of the solvent could not be removed, and thus pyrolysis yielded a very porous structure. It thus was not suitable for use as an impregnant. It should be noted that diethynylbenzene, from which "H resin" is made, can polymerize explosively when heated. Thus, its use as a homopolymerizable liquid impregnant is highly unlikely.

SUMMARY OF THE INVENTION

The general objective of this invention is to provide a class of low melting, homopolymerizable aromatic hydrocarbons suitable for use as impregnants in the formation of 3-D carbon-carbon structures such as Intercontinental Ballistic Missile nose cones.

In accomplishing this objective, while avoiding the disadvantages of the prior art and at the same time retaining the advantages of said art, we have invented diethynyl aromatic compounds of the type illustrated below which exhibit low melting points, are homopolymerizable at relatively low temperatures, and can be used as impregnant to form 3-Dimensional carbon-carbon composites which char efficiently in high yield. These compounds have the following chemical structures.

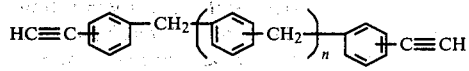

where n may be 0, 1, 2, 3, or 4.

Compounds of this invention can be prepared by the VIELSMEIER process or by a variety of other processes.

It is therefore an objective of this invention to provide new and improved low melting homopolymerizable hydrocarbons. A second objective of this invention is to provide very fluid compounds which when melted can effectively penetrate the pores of porous or woven structures. A third objective of this invention is to provide impregnants which do not outgas when cured. A fourth objective of this invention is to provide curable impregnants which char efficiently after cure. A fifth objective of this invention is to provide a homopolymerizable high char forming impregnant which cannot soften and exude from an impregnated matrix when the cured impregnated matrix is pyrolyzed and pyrolysis gas pressures are generated.

That we have accomplished the above stated objectives, while avoiding the disadvantages of the prior art and retaining most, if not all, of the advantages of said art will be apparent upon reference to the following detailed description of the invention.

DETAILED DESCRIPTION OF THE INVENTION

We have invented several exceptionally low viscosity, homopolymerizable diethynyl substituted compounds that are suitable for use as impregnants which char efficiently after relatively low temperature cures. Our compounds have the following structure:

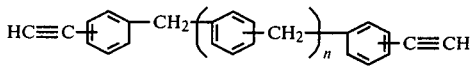

where n may range from 0 to about 4.

In contrast to compounds of the prior art, which either do not cure or only cure at very high temperatures, our compounds can be homopolymerized into an infusible resin after impregnation at temperatures ranging from 110° C. to above 200° C. without the evolution of gas.

The low viscosity of our compounds renders them exceptionally suitable for use as impregnants for fibrous graphite cloths and the formation of ablative composites. When cured, samples of our impregnants exhibit as high as 91% char yield as measured by thermo gravimetric analysis (TGA). The high char yields of our compounds are attributed to the absence of elements such as nitrogen, oxygen, sulfur, phosphorus and various halogens in their structures and to their ability to homopolymerize into polyaromatic hydrocarbon matrices.

A preferred compound of our invention is 4,4'-diethynyldiphenylmethane which melts at about 66° C., forming a colorless low viscosity fluid. This material polymerizes into a non-tacky-state resin in about 20 minutes when heated at 180° C.; at 170° C., it takes about 45 minutes to polymerize to a non-tacky state; at 160° C., it takes an hour and 20 minutes; at 150° C., the resin polymerizes in about 2 hours; at 120° C., eight to twelve hours are required to achieve a non-tacky-state resin; and at 110° C. from sixteen to twenty hours are required. Essentially then, the polymerization rate can be controlled by careful temperature control, and runaway explosive polymerization, characteristic of diethynylbenzene polymerizations, need not be a problem.

Thermogravimetric analyses, of the resin described above, showed that at temperatures between 210° C. and 800° C. it lost only 9% of its weight. Thus, the char yield of this material was 91%.

Nuclear magnetic resonance analysis clearly confirmed its structure to be

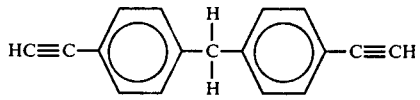

and differential scanning calorimetry indicated an onset of the cure exotherm at about 150° C. and a maximum cure exotherm at 205° C. Slow polymerization, below 190° C. occurs, but is not evident in the DSC Analysis.

The meta isomer of our invention, when n is o, is also a preferred species in that its melting point is lower than that exhibited by the para isomer described above.

Specific examples of synthetic procedures used to prepare our invention and its intermediates are shown below.

EXAMPLE I

Preparation of 4,4' Diacetyldiphenylmethane

Aluminum trichloride ($AlCl_3$) (1 lb.) and 1,2-dichlorethane (650 ml.) were placed into a 2 l. flask. Acetic anhydride (158 ml.) was added dropwise with vigorous stirring and ice bath cooling. Diphenylmethane (65 g, 0.386 moles) in 1,2-dichlorethane (250 ml) was added dropwise over a ½ hr. period. After 2 hr. at 0° C., then 1½ hr. at reflux, the complex was decomposed in HCl/ice. After water washing the organic layer, the solvent was distilled, giving a product which when recrystallized from ethanol weighed 52 g (53% yield). Its melting point was 90°–93° C.

EXAMPLE II

Preparation of 4,4-diethynyldiphenylmethane by the Vielsmeier Process

Dimethylformamide (DMF, 30 ml.) was placed into a 250 ml. flask and 21 ml. of $POCl_3$ was added with stirring and cooling. Diacetyldiphenylmethane (12.5 g) in DMF (100 ml) was added slowly then the reaction mixture was allowed to set overnight. The product was poured into saturated $NaHCO_3$ solution (1500 ml). Filtration provided 21 g of crude product. The aqueous phase was extracted with toluene and the solid was triturated with toluene. The toluene was distilled off and the gummy product was poured into isopropyl alcohol. A finely divided solid (6.2 g, m.p. 138°–142° C.) separated. Its I.R. spectrum was similar to that of α-chlorocinnamaldehyde, thus, it was the anticipated 4,4'-methylene bis (α-chloro) cinnamaldehyde. Six grams of the compound was dissolved in p-dioxane and this was added to a reluxing solution of NaOH (93 g.) in water (20 ml.) Additional NaOH (1½ g) was added and the mixture was heated at reflux for 1 hour under argon. After cooling, the dioxane and water were removed in a rotary evaporator and the residue was extracted with ether and hexane. Solvent removal yielded a solid product, which after recrystallization from ethanol melted at 60°–65° C.

The product was chromatograhed on $Al_2O_3$ using hexane as the eluent. Evaporation of the hexane provided 1.0 g. of crystalline product, M.P. 66°–67° C. The product proved to be pure 4,4'-diethynyldiphenylmethane.

EXAMPLE III

Preparation of Bis (ethynylbenzyl)benzene

Isophthaloyl chloride (203 g., 1 mole) was added dropwise with continuous stirring and heating to one liter of toluene containing two moles of $AlCl_3$. Upon completion of the reaction as evidenced by the low level of HCl evolution, the reaction mixture was poured over ice/HCl. The organic phase was separated, washed repeatedly with water, and distilled to remove the unreacted toluene. The bis (methylbenzyl)benzene then was isolated and oxidized with chromic acid to give bis (carboxybenzoyl)benzene. Subsequent reduction with sodium borohydride provided bis (carboxybenzyl)benzene which was converted to the bis (acetylbenzyl)benzene by treatment with a 4 molar excess of methyl lithium. Conversion of the bis acetyl compound to the corresponding bis ethynyl compound was achieved through the well known Vielsmeier process. The overall yield of the acetylene compound was 8%.

It can be seen from the above examples that the principal limitation to our invention is the high cost of our compounds which results from the relatively low yields of our synthetic procedures. However, we anticipate the development of improved synthetic routes which should increase the yields and thereby reduce the cost of our compounds significantly.

INDUSTRIAL APPLICABILITY

Compounds prepared in accordance with our invention may be utilized as impregnants for fibrous graphite cloths to form composites which char efficiently and therefore produce good ablative materials for reentry applications.

The low viscosity of these materials coupled with the relative low curing temperatures improves their utility for large scale fabrication operations.

High reliability is obtained by the use of relatively pure materials in contrast to the variable composition coal tar and petroleum pitches of the prior art.

Having completely disclosed our invention and provided teachings which enable others to make and utilize the same, the scope of our claims may now be understood as follows.

What is claimed is:

1. Compounds having melting points of less than 150° C. which homopolymerize at temperatures below 200° C. and char efficiently whose structural formulas are:

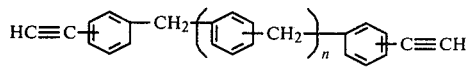

wherein n may range from 0 to 4.

2. A compound of claim 1 wherein n is 0.

3. A compound of claim 1 wherein n is 0 and the acetylene substituents on the phenyl rings are in a para position relative to the methylene group which separates said phenyl rings.

4. A homopolymerizable diethynyl substituted aromatic compound which melts at a temperature below 100° C. and whose structure is selected from the group consisting of

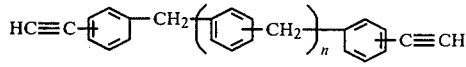

wherein n may range from 0 to about 4.

5. A compound of claim 4 wherein n is 0.

6. A compound of claim 1 wherein n is 0 and the acetylene substituents on the phenyl rings are in a meta position relative to the methylene group which separates said phenyl rings.

7. A compound of claim 1 wherein n is 0 and one of the acetylene substituents on one phenyl ring is in a meta position and the second acetylene substituent is in the para position on the other phenyl ring with respect to the methylene group which separates said phenyl rings.

* * * * *